(12) United States Patent
Bologna et al.

(10) Patent No.: US 8,796,488 B2
(45) Date of Patent: Aug. 5, 2014

(54) PROCESS FOR THE PREPARATION OF LACOSAMIDE

(75) Inventors: Alberto Bologna, Trovo (IT); Patrizia Castoldi, Lainate (IT); Domenico Vergani, Biassono (IT); Giorgio Bertolini, Sesto San Giovanni (IT)

(73) Assignee: Euticals S.p.A., Milan (IT)

( * ) Notice: Subject to any disclaimer, the term of this patent is extended or adjusted under 35 U.S.C. 154(b) by 116 days.

(21) Appl. No.: 13/575,152

(22) PCT Filed: Dec. 22, 2010

(86) PCT No.: PCT/IB2010/056014
§ 371 (c)(1),
(2), (4) Date: Oct. 9, 2012

(87) PCT Pub. No.: WO2011/092559
PCT Pub. Date: Aug. 4, 2011

(65) Prior Publication Data
US 2013/0030216 A1     Jan. 31, 2013

(30) Foreign Application Priority Data
Jan. 29, 2010 (IT) .............................. MI2010A0127

(51) Int. Cl.
*C07C 233/06* (2006.01)
*C07C 231/14* (2006.01)
*C07C 231/20* (2006.01)
*C07C 231/12* (2006.01)
*C07C 237/22* (2006.01)
*C07C 237/06* (2006.01)

(52) U.S. Cl.
CPC ............. *C07C 237/22* (2013.01); *C07C 237/06* (2013.01); *C07C 231/20* (2013.01); *C07B 2200/07* (2013.01); *C07C 231/12* (2013.01)
USPC .......................................... 564/158; 564/196

(58) Field of Classification Search
CPC ........................... C07C 231/14; C07C 233/06
USPC ................................... 564/158, 196
See application file for complete search history.

(56) References Cited

U.S. PATENT DOCUMENTS

| 5,773,475 | A | 6/1998 | Kohn |
| RE38,551 | E | 7/2004 | Kohn |
| 7,884,134 | B2 * | 2/2011 | Riedner et al. ................ 514/616 |
| 8,093,426 | B2 * | 1/2012 | Madhra et al. ................ 564/165 |

FOREIGN PATENT DOCUMENTS

| EP | 2067765 | 6/2009 |
| WO | WO2006037574 | 4/2006 |
| WO | WO2010/052011 | 5/2010 |

OTHER PUBLICATIONS

Berge et al, J. Pharm. Sci, 66(1):1-19, 1977.*
Andurkar S.V., et al., Tetrahedron: Asymmetry, vol. 9, p. 3841-3854, 1998.
Choi, D., et al., Journal of Medicinal Chemistry, vol. 39, p. 1907-1916, 1996.
International Search Report for PCT/IB2010/056014 of Mar. 22, 2011.
IPRP for PCT/IB2010/056014 of Sep. 22, 2011.
Itlian Search Report for IT/MI2010/0127 of Jun. 3, 2010.

* cited by examiner

*Primary Examiner* — Shailendra Kumar
(74) *Attorney, Agent, or Firm* — Hueschen and Sage

(57) ABSTRACT

A novel process for the synthesis of Lacosamide using D,L-serine as starting material is described, where the methylation reaction of hydroxyl is carried out using an inexpensive base such as NaOH and an inexpensive alkylating agent, non-toxic and non-carcinogenic, such as methyl p-toluenesulfonate; the R enantiomer is isolated from the racemic mixture of Lacosamide after selective hydrolysis of the acetamide, salification of the racemic mixture with a chiral acid (HX*) in an organic solvent, resolution of the diastereoisomeric mixture, preferably by precipitation of the R enantiomer, and subsequent acetylation of the optically pure intermediate.

49 Claims, 1 Drawing Sheet

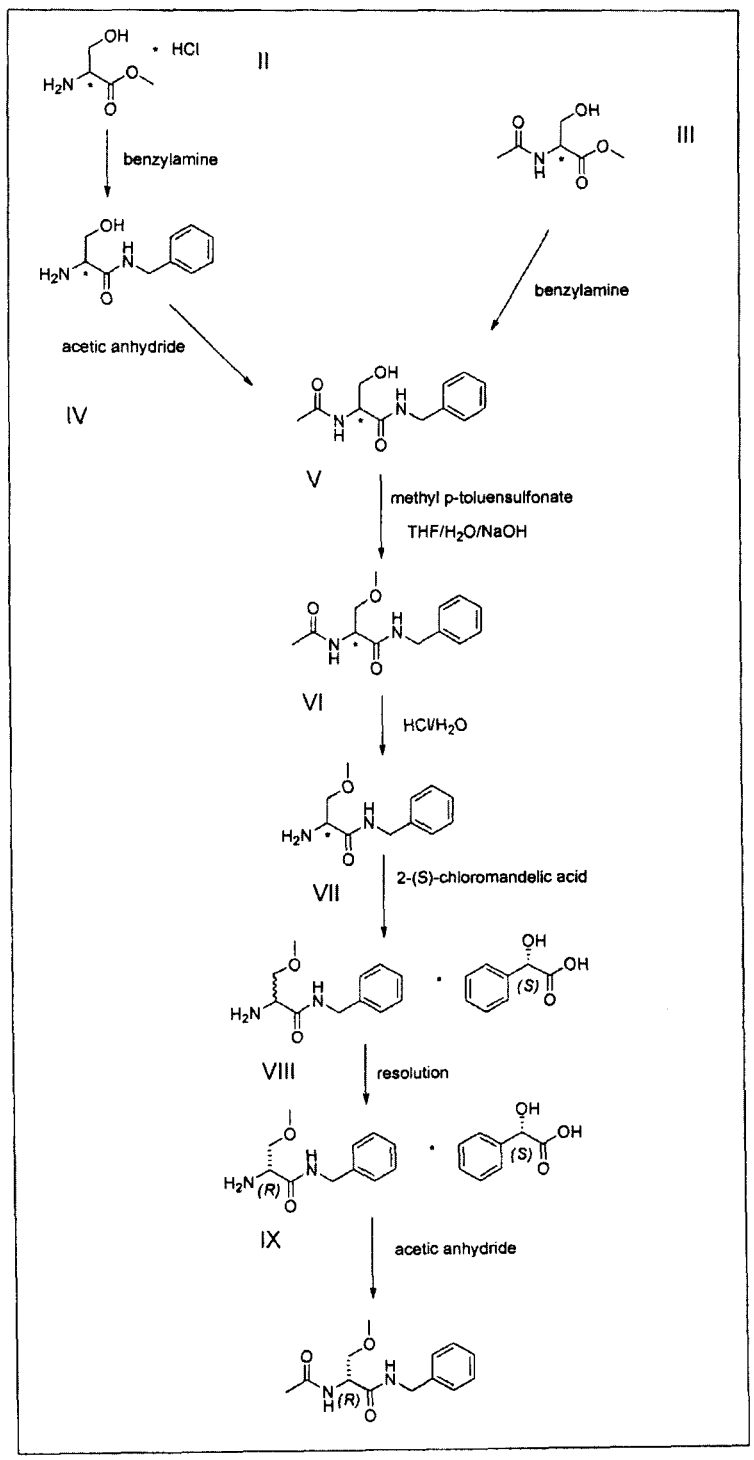

PROCESS FOR THE PREPARATION OF LACOSAMIDE

This application is a 371 of PCT/IB2010/056014, filed Dec. 22, 2010.

The present invention relates to a novel process for the preparation of (2R)-2-(acetylamino)-N-benzyl-3-methoxypropanamide, an active ingredient used for curing neuropathies, known by the name of Lacosamide and represented by the formula of structure I indicated below

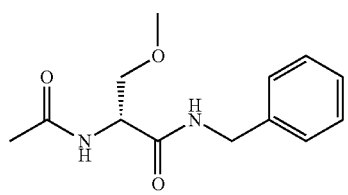

I

The process according to the present invention is carried out starting from D,L-serine methylester, i.e. the molecule with the formula of structure II indicated below,

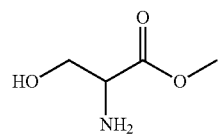

II which is preferably used in the form of hydrochloride.

Alternatively, it can be carried out starting from the acetamide of D,L-serine methylester, i.e. the molecule corresponding to the formula of structure III, also indicated below:

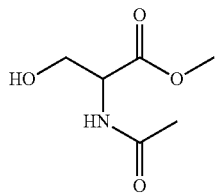

III

PRIOR ART

Lacosamide is an active ingredient used in the pain therapy and for curing various diseases of the nervous system among which epilepsy. Though the action mechanism is not completely clear, it seems that it operates on the sodium channels of the neurons reducing their activity. Furthermore, Lacosamide is thought to be involved in the restoration of the damaged neurons.

The product is described and claimed in the U.S. Pat. No. RE38,551. Three different synthesis methods which use D-serine as starting material and methyl iodide and silver oxide for the methylation of the OH are also indicated in this document. An alternative method for the synthesis of Lacosamide is that described in the patent application WO 2006/037574 where, starting from N-Boc protected D-serine, the methylation reaction of hydroxyl is carried out using butyllithium and an alkylating agent.

A further alternative synthesis method is that indicated in the patent application EP 2067765 where, before the methylation of hydroxyl, the amino group is protected with a hindered group such as the trityl.

All the preparation methods described up to now use D-serine as starting material and use expensive reagents such as silver oxide or butyllithium or hindered protective groups with the aim of minimising the racemisation of the product. The reason lies in the fact that methods for the resolution of racemic mixtures of Lacosamide have not yet been developed up to date and the purification of the R enantiomer is described as extremely difficult.

DESCRIPTION OF THE INVENTION

The present invention relates to a novel synthesis of Lacosamide which uses D,L-serine as starting material, where the methylation reaction of hydroxyl is carried out using an inexpensive base such as NaOH and an inexpensive alkylating agent, non-toxic and non-carcinogenic, such as the methyl p-toluenesulfonate; the R enantiomer is isolated from the racemic mixture of Lacosamide after selective hydrolysis of the acetamide, salification of the racemic mixture with a chiral acid (HX*) in an organic solvent, resolution of the diastereoisomeric mixture, preferably by precipitation of the R enantiomer, and subsequent acetylation of the optically pure intermediate.

The present invention relates to a novel synthesis of Lacosamide which uses D,L-serine methyl ester, of formula II, as starting material, preferably in the form of hydrochloride, easily obtainable from D,L-serine by the extensively described methods.

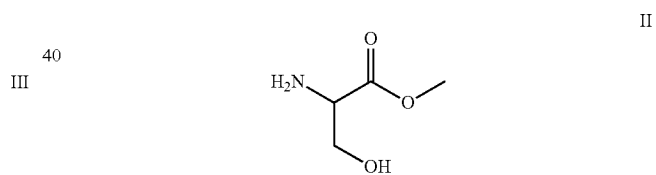

II

The product of formula II is converted into the product of formula V by reaction first using benzylamine and subsequently using acetic anhydride (or an acetyl halide, preferably acetyl chloride, or using a mixed anhydride), according to the following scheme.

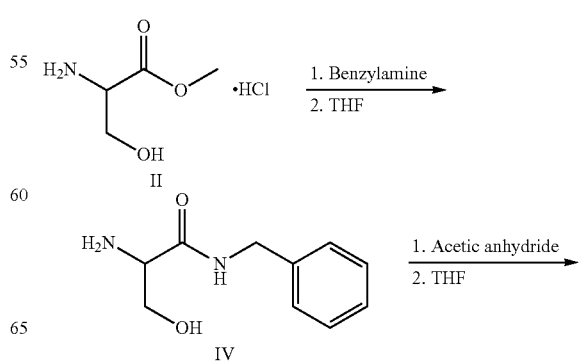

IV

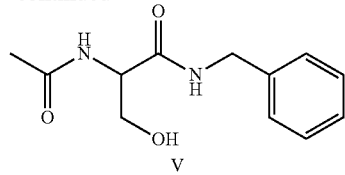

V

The first reaction is preferably carried out directly in benzylamine (from 2 to 10 equivalents), or in an aprotic polar solvent, such as for example THF, at a temperature comprised between 0° C. and the reflux temperature, preferably at 30-40° C.; the second reaction is carried out by reacting the compound IV with acetic anhydride (or with an acetyl halide, preferably acetyl chloride) in an aprotic polar solvent, such as for example THF, at a temperature preferably comprised between 10 and 40° C., preferably between 15 and 30° C., even more preferably between 20 and 25° C.

Alternatively the compound V can be prepared from the D,L-serine methyl ester acetamide of formula III, available in the market, by reaction with benzylamine; also in this case the reaction is preferably carried out directly in benzylamine (from 2 to 10 equivalents), or in a suitable organic solvent, preferably an aprotic polar solvent, such as for example THF, at a temperature comprised between 0° C. and the reflux temperature of the solvent, preferably at about 65° C.

or inorganic base, at a temperature preferably comprised between 20 and 40° C., preferably between 30 and 35° C. The solvent is preferably an aprotic polar solvent, such as for example THF. The alkylating agent is preferably selected from among methyl iodide, dimethyl sulfate, methyl mesylate and methyl para-toluenesulfonate; it is preferably methyl para-toluenesulfonate. The organic base is preferably selected from among tertiary amines $NR_1R_2R_3$, where $R_1$, $R_2$ and $R_3$ the same or different from each other, are linear or branched $C_1$-$C_4$ alkyl chains; the preferred tertiary amine is triethylamine. The inorganic base is preferably a hydroxide of an alkaline-earth or alkaline metal, such as KOH or NaOH.

The inorganic base can be used in aqueous solution. In case of the use of an inorganic base, it is preferable to use also a phase transfer catalyst for accelerating the reaction; said phase transfer catalyst is preferably a salt of tetrabutylammonium having hydroxide, hydrogen sulfate, chlorine, bromine or iodine as the counterion.

The compound VI, racemic Lacosamide, is converted into the compound VII by hydrolysis in aqueous solution with an inorganic mineral acid, preferably HCl, at a pH preferably comprised between 0 and 2; such hydrolysis reaction is preferably carried out at the reflux temperature. The compound VII is then extracted, after the neutralization of the acid, in an organic solvent, preferably in an aprotic apolar solvent, such as for example $CH_2Cl_2$, $CHCl_3$ or $C_2H_4Cl_2$.

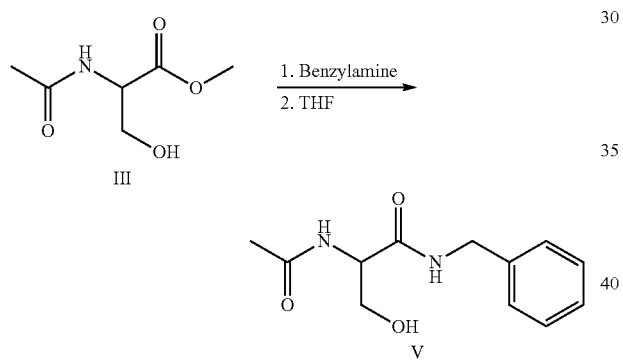

The compound V is converted into the compound VI by methylating the hydroxyl present in the molecule.

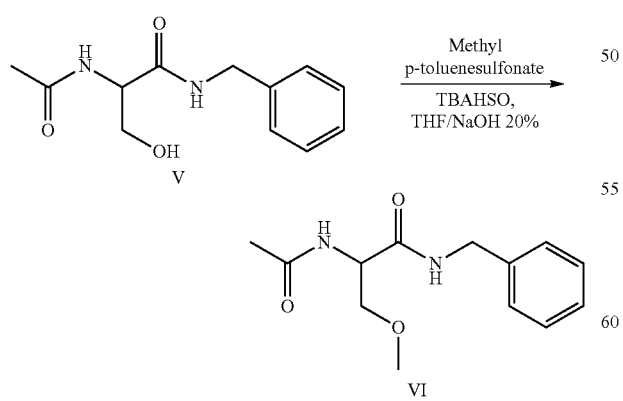

The methylation reaction can be carried out by dissolving the compound V in a suitable organic solvent and placing it at contact with an alkylating agent in the presence of an organic

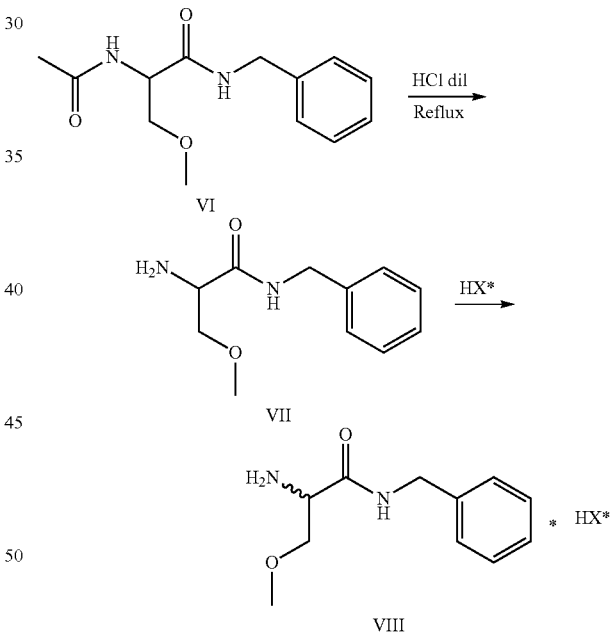

The compound VII is then precipitated as salt VIII with a chiral acid (HX*), preferably D, such as for example dibenzoyl tartaric, tartaric, camphorsulfonic, mandelic, 2-chloromandelic, 3-chloromandelic, 4-chloromandelic acid; for the purposes of the present invention, the acid is preferably 2-chloromandelic, even more preferably 2-(S)-chloromandelic acid. The chiral acid is used at an amount preferably comprised between 0.5 and 1.5 equivalents. The precipitation is preferably carried out in an aprotic polar organic solvent, such as for example ethyl acetate or isopropyl acetate, even more preferably isopropyl acetate. The salt VIII quantitatively precipitates from this solvent as a diastereoisomeric mixture. The salt VIII thus obtained is further solubilised in a suitable mixture of solvents capable of allowing selective precipitation of only one enantiomer, preferably the desired enantiomer IX alone. Such mixture of solvents is constituted by an aprotic organic solvent and a protic solvent. The aprotic organic solvent is preferably selected from among THF, methyl-THF, ethyl acetate, isopropyl acetate; aprotic polar organic solvents, such as ethyl acetate and isopropyl acetate are however preferred. The protic solvent is instead preferably selected from among $C_1$-$C_4$ alcohols (for example, methanol, ethanol, isopropanol, n-butanol, i-butanol, s-butanol) and water; preferably, a mixture of ethyl acetate and ethanol is used. According to a further preferred aspect of the invention, 10 to 40 volumes of aprotic organic solvent per volume of protic solvent are used.

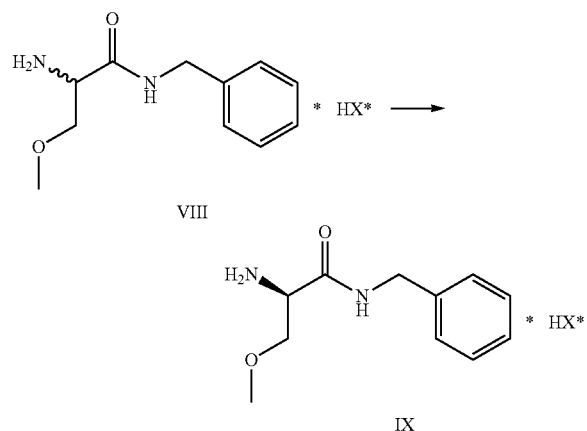

The compound IX is acetylated in the presence of an acylating agent in a suitable organic solvent, preferably apolar aprotic, even more preferably an ether, in the presence of an amount of water comprised between 0 and 50% by weight with respect to the compound IX, preferably between 5 and 20%, to obtain Lacosamide. The $C_2$-$C_8$ ethers, such as for example the methyl tert-butyl ether, are particularly preferred for the purposes of the present invention; the acetic anhydride is the preferred acylating agent (alternatively an acetyl halide, preferably acetyl chloride, can be used); the acylation reaction is preferably carried out between 0 and 40° C., preferably between 20 and 25° C. Further objects of the present invention, are represented by the salts of formula VIII and IX

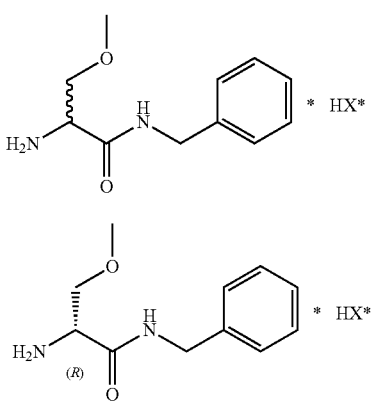

where HX* has the previously listed meanings and, in the preferred aspect of the invention, it is 2-(S)-chloro-mandelic acid.

The complete scheme of the process according to the present invention is indicated in FIG. 1 with reference to the case in which the chiral acid HX* is 2-(S)-chloro-mandelic acid.

EXAMPLE 1

Synthesis of V Starting from III

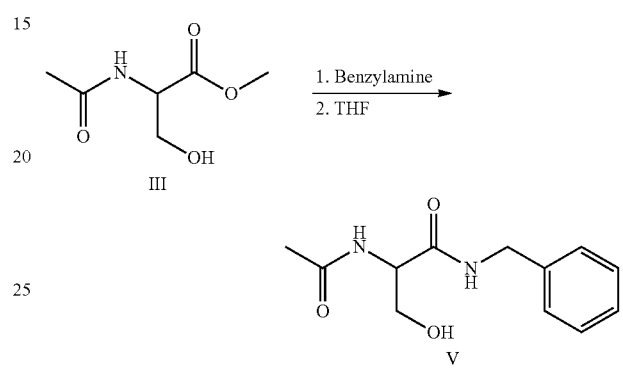

100 g of compound III and 332 g of benzylamine are loaded into a 1 liter reactor provided with a mechanical stirrer, reflux condenser, thermometer and placed in nitrogen atmosphere. The mixture is heated to 65° C. and it is kept under stirring at this temperature for 12 hours. It is distilled under vacuum to remove the excess benzylamine. It is cooled to about 55-60° C. and 50 ml of THF are added. Then, it is cooled to 20° C. and the resulting solid is filtered then it is dried under vacuum at 40° C. 123.2 g of compound V are obtained. 84% molar yield

EXAMPLE 2

Synthesis of VI from V

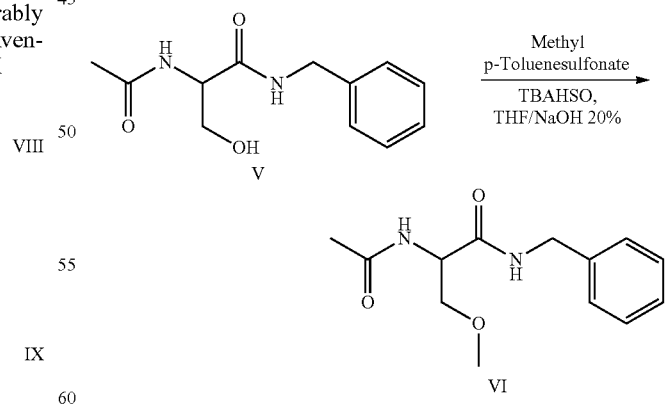

148 g of compound V, 7.4 g of tetrabutylammonium sulfate, 740 ml of THF, 350 g of methyl para-toluenesulfonate and 440 g of 20% sodium hydroxide are loaded into a 3 liter reactor provided with a mechanical stirrer, reflux condenser, thermometer and placed in nitrogen atmosphere. The mixture thus obtained is heated to 35° C. and kept under stiffing at this temperature for 4 hours. It is then cooled to 20-25° C. and 165 g of 28% ammonium hydroxide are added. It is cooled to 5° C. and the pH is brought to 7 using hydrochloric acid.

It is distilled under vacuum to remove the THF and it is diluted using 1 liter of water.

It is extracted 4 times using 500 ml of dichloromethane then organic phases are combined and distilled to small volume. Dichloromethane is substituted with 600 ml of isopropyl acetate. The resulting suspension is filtered and the resulting solid is washed with isopropyl acetate and dried under vacuum at 40° C. 115 g of compound VI are obtained. 73% molar yield.

EXAMPLE 3

Synthesis of VIII from VI

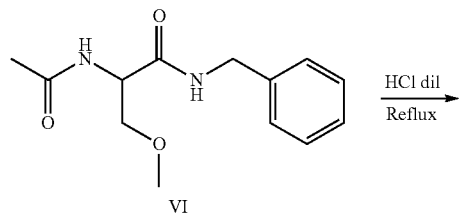

VI

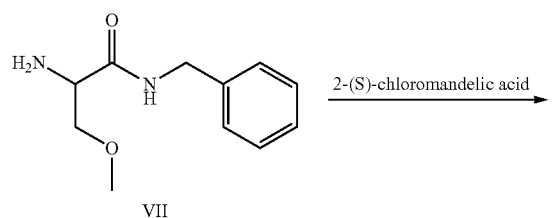

VII

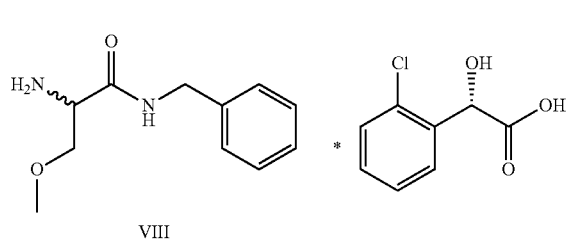

VIII 63.5 g of compound VI, 850 ml of water and 65 g of 37% HCl are loaded into a 2 liter reactor provided with a mechanical stirrer, reflux condenser, thermometer and inerted with nitrogen. The mixture is heated to reflux and it is kept under stirring for 6 hours, then it is cooled to 20-25° C. The pH is corrected to 11.5±0.5 with 30% sodium hydroxide. The resulting mixture is extracted 2 times with 300 ml of dichloromethane. The combined organic phases are concentrated to small volume, 300 ml of ethyl acetate and 35 g of 2-(S)-chloromandelic acid are added. Half of the solvent is distilled and it is left under stirring at room temperature up to complete precipitation. The solid is filtered and dried under vacuum at 40° C. 84.3 g of the diastereoisomeric mixture VIII are obtained. 84.1% molar yield

EXAMPLE 4

Resolution of the Diastereoisomeric Mixture VIII to Obtain IX

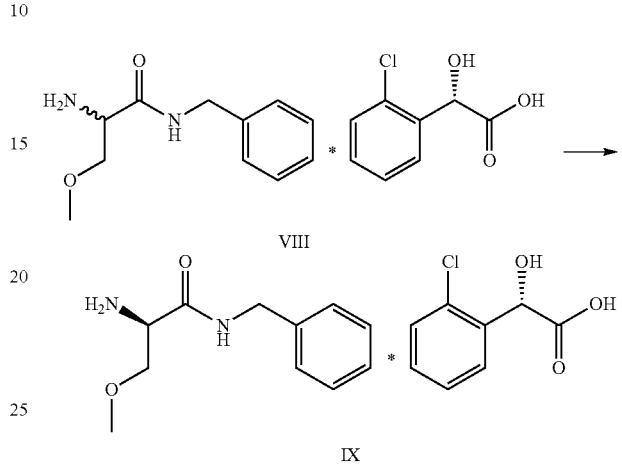

120 g of the racemic diastereoisomeric mixture VIII, 3.5 liters of ethyl acetate and 300 ml of ethanol are loaded into a 5 liter reactor provided with a mechanical stirrer, reflux condenser, thermometer and placed in nitrogen atmosphere. It is heated up to complete dissolution then it is cooled slowly up to 20° C. and it is maintained under stirring for 5 hours at this temperature. The resulting solid is filtered and dried 61 g of compound IX are obtained with a 37% molar yield on the racemate.

EXAMPLE 5

Synthesis of I from IX

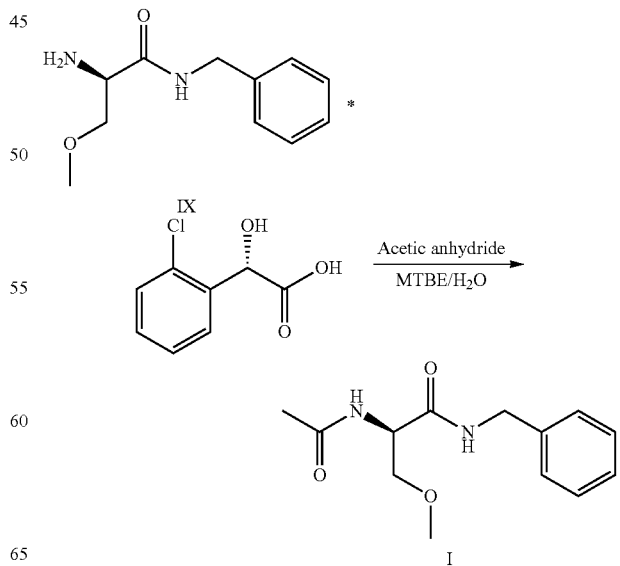

35 g of compound VIII, 700 ml of methyl tent-butyl ether and 5 ml of water are loaded into a 1 liter reactor provided with a mechanical stirrer, reflux condenser, thermometer and inerted with nitrogen. It is cooled to 10-15° C. and 10 g of acetic anhydride are dropped into the reaction mixture. It is kept under stirring for 2 hours at room temperature, then the resulting solid which is dried under vacuum at 40° C. is filtered. 19.5 g of Lacosamide are obtained. 88% molar yield.

EXAMPLE 6

Synthesis of V from II

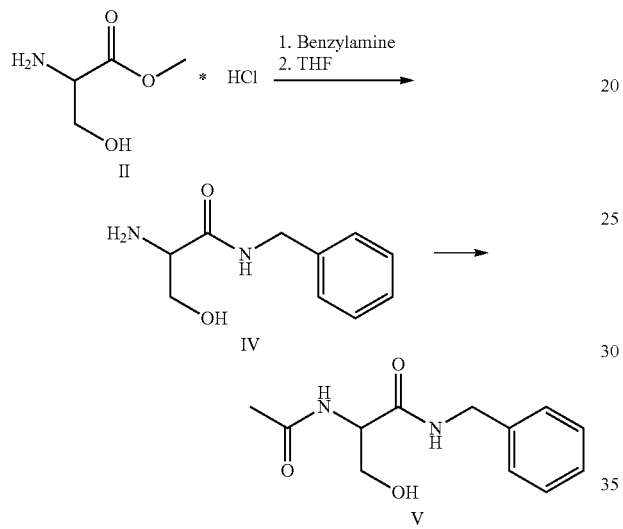

100 g of compound II and 330 g of benzylamine are loaded into a 1 liter reactor provided with a mechanical stirrer, reflux condenser, thermometer and inerted with nitrogen. The mixture is heated to 35° C. and it is kept under stirring at this temperature for 22 hours. It is distilled under vacuum up to the removal of benzylamine and 1.2 liters of THF are added. It is heated until a limpid solution is obtained and it is cooled slowly up to room temperature. The solid is filtered and 65 g of acetic anhydride are slowly added to the resulting solution. It is concentrated up to half volume and it is cooled slowly to 0-5° C. The resulting solid is filtered and dried under vacuum at 40° C. 106 g of compound V are obtained. 70% molar yield.

The invention claimed is:

1. A process for the synthesis of Lacosamide comprising the following steps:

(a) hydroxymethylation of a compound of formula V

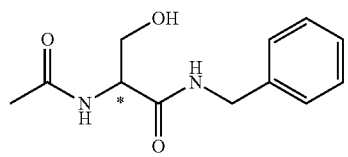

to obtain a compound of formula VI

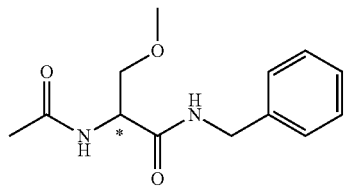

(b) hydrolysis of the compound of formula VI to obtain a compound of formula VII

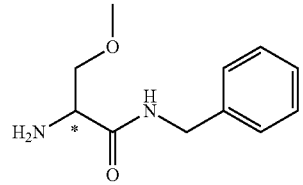

(c) salification of the compound of formula VII with a chiral acid (HX*) in an organic solvent, to obtain a diastereoisomeric mixture VIII

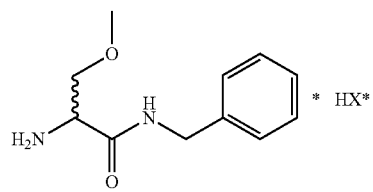

(d) resolution of the diastereoisomeric mixture VIII to obtain a salt IX

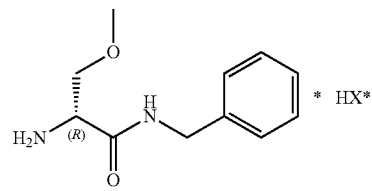

(e) conversion of the salt IX into Lacosamide.

2. The process according to claim 1, wherein the hydroxymethylation (a) is carried out by reacting the compound of formula V with an alkylating agent in the presence of a base.

3. The process according to claim 2, wherein the alkylating agent is selected from methyl iodide, dimethyl sulfate, methyl mesylate, and methyl para-toluenesulfonate.

4. The process according to claim 3, wherein the alkylating agent is methyl para-toluenesulfonate.

5. The process according to claim 2, wherein the base is an organic base and/or an inorganic base.

6. The process according to claim 5, wherein the organic base is a compound of formula $NR_1R_2R_3$ wherein $R_1$, $R_2$ and $R_3$, which may be the same or different, represent linear or branched $C_1$-$C_4$ alkyl chains.

7. The process according to claim 6, wherein the organic base is triethylamine.

8. The process according to claim 5, wherein the inorganic base is a hydroxide of an alkaline earth or alkaline metal.

9. The process according to claim 8, wherein the inorganic base is KOH or NaOH.

10. The process according to claim 1, wherein the hydroxymethylation (a) is carried out at a temperature between 20° C. and 40° C.

11. The process according to claim 10, wherein the hydroxymethylation (a) is carried out at a temperature between 30° C. and 35° C.

12. The process according to claim 1, wherein the hydroxymethylation (a) is carried out in an aprotic polar solvent.

13. The process according to claim 12, wherein the hydroxymethylation (a) is carried out in THF.

14. The process according to claim 1, wherein hydrolysis (b) is carried out in the presence of a mineral acid.

15. The process according to claim 14, wherein hydrolysis (b) is carried out in the presence of hydrochloric acid.

16. The process according to claim 1, wherein the organic solvent is an aprotic polar organic solvent.

17. The process according to claim 1, wherein the chiral acid (HX*) is selected from dibenzoyl tartaric acid, tartaric acid, camphorsulfonic acid, mandelic acid, 2-chloromandelic acid, 3-chloromandelic acid, and 4-chloromandelic acid.

18. The process according to claim 17, wherein the chiral acid (HX*) is 2-(S)-chloromandelic acid.

19. The process according to claim 1, wherein between 0.5 and 1.5 equivalents of the chiral acid is used.

20. The process according to claim 16, wherein the aprotic polar organic solvent is selected from ethyl acetate, isopropyl acetate, tetrahydrofuran, acetone, tetrahydrofuran, and methyl-tetrahydrofuran.

21. The process according to claim 20, wherein the aprotic polar organic solvent is isopropyl acetate.

22. The process according to claim 1, wherein the resolution (d) of the diastereoisomeric mixture VIII is carried out by precipitation from a mixture of at least one aprotic organic solvent and at least one protic solvent.

23. The process according to claim 22, wherein the at least one aprotic organic solvent is selected from THF, methyl-THF, ethyl acetate, isopropyl acetate, and/or the at least one protic solvent is selected from water and $C_1$-$C_4$ alcohols.

24. The process according to claim 23, wherein the at least one aprotic organic solvent is selected from ethyl acetate and isopropyl acetate.

25. The process according to claim 23, wherein the at least one protic solvent is selected from methanol, ethanol, isopropanol, n-butanol, i-butanol and s-butanol.

26. The process according to claim 22, wherein the mixture consists of ethyl acetate and ethanol.

27. The process according to claim 22, wherein 10 to 40 volumes of aprotic organic solvent per volume of protic solvent are used.

28. The process according to claim 1, wherein step (e) is carried out in the presence of an acylating agent in at least one organic solvent, optionally mixed with water.

29. The process according to claim 28, wherein the at least one organic solvent is an apolar aprotic solvent.

30. The process according to claim 28, wherein the acylating agent is acetic anhydride or an acetyl halide.

31. The process according to claim 28, wherein step (e) is carried out at a temperature between 0 and 40° C.

32. The process according to claim 31, wherein step (e) is carried out at a temperature between 20 and 25° C.

33. The process according to claim 28, wherein the at least one organic solvent is an ether.

34. The process according to claim 33, wherein the at least one organic solvent is a $C_2$-$C_8$ ether.

35. The process according to claim 34, wherein the at least one organic solvent is methyl tert-butyl ether.

36. The process according to claim 28, wherein water is present in an amount between 0 and 50% by weight with respect to the compound IX.

37. The process according to claim 36, wherein water is present in an amount between 5 and 20% by weight with respect to the compound IX.

38. The process according to claim 1, wherein the compound V is obtained by:

(aa) amidation of a compound of formula II with benzylamine

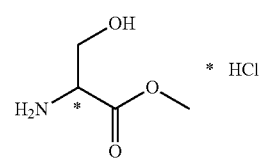

to obtain a compound IV

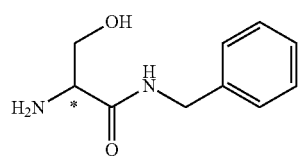

(bb) acylation of the compound of formula IV thus obtained to obtain the compound V

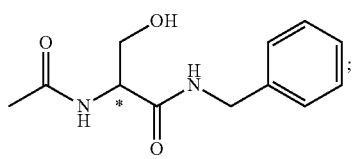

or (cc) amidation of a compound of formula III

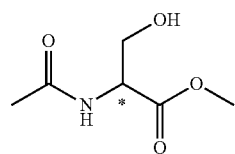

to obtain the compound of formula V

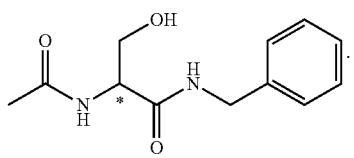

39. The process according to claim 38, wherein from 2 to 10 equivalents of benzylamine are used.

40. The process according to claim 38, wherein step (aa) is carried out at a temperature between 0° C. and the reflux temperature of the solvent; step (bb) is carried out at a temperature between 10° C. and 40° C.; and/or step (cc) is carried out at a temperature between 0° C. and the reflux temperature of the solvent.

41. The process according to claim 40, wherein step (aa) is carried out at a temperature between 30° C. and 40° C.

42. The process according to claim 40, wherein step (bb) is carried out at a temperature between 15 and 30° C.

43. The process according to claim 42, wherein step (bb) is carried out at a temperature between 20 and 25° C.

44. The process according to claim 40, wherein step (cc) is carried out at 65° C.

45. The process according to claim 38, wherein step (aa) is carried out in benzylamine or in an aprotic polar solvent; step (bb) is carried out in the presence of acetic anhydride, a mixed anhydride and/or an acetyl halide, in an aprotic polar solvent; and/or step (cc) is carried out in benzylamine or in an aprotic polar solvent.

46. The process according to claim 45, wherein step (aa) is carried out in THF.

47. The process according to claim 45, wherein step (bb) is carried out in the presence of acetyl chloride.

48. The process according to claim 45, wherein step (bb) is carried out in THF.

49. The process according to claim 45, wherein step (cc) is carried out in THF.

* * * * *